United States Patent [19]

Von Weissenfluh

[11] Patent Number: 4,889,489

[45] Date of Patent: Dec. 26, 1989

[54] DEVICE WITH SPINDLE AND GRINDING DISK, PARTICULARY FOR DENTISTS, AND METHOD FOR THE MANUFACTURE THEREOF

[75] Inventor: Beat Von Weissenfluh, Gentilino, Switzerland

[73] Assignee: Hawe-Neos Dental Dr. H.v. Weissenfluh AG, Switzerland

[21] Appl. No.: 168,007

[22] PCT Filed: Apr. 7, 1987

[86] PCT No.: PCT/CH87/00039

§ 371 Date: Feb. 25, 1988

§ 102(e) Date: Feb. 25, 1988

[87] PCT Pub. No.: WO88/00029

PCT Pub. Date: Jan. 14, 1988

[30] Foreign Application Priority Data

Jun. 26, 1986 [CH] Switzerland .......................... 2592/86

[51] Int. Cl.$^4$ ................................................. A61C 3/06
[52] U.S. Cl. .................................................... 433/134
[58] Field of Search ............. 433/134; 51/209 R, 594, 51/379, 389, 358, 376

[56] References Cited

U.S. PATENT DOCUMENTS 4,601,661 7/1986 Du Be et al. ..................... 433/136
4,624,876 11/1986 Nevin .................................. 433/134

FOREIGN PATENT DOCUMENTS 0044701 1/1982 European Pat. Off. .
1949505 4/1971 Fed. Rep. of Germany .
3305644 8/1984 Fed. Rep. of Germany .

Primary Examiner—Robert Peshock
Attorney, Agent, or Firm—Ostrolenk, Faber, Gerb & Soffen

[57] ABSTRACT

A combination of a rotatable spindle and grinding disk, and a method of assembly thereof. The spindle has an end with radial slits. The grinding disk has a hub which rests on the end face of the spindle. A portion protruding from the end face of the spindle has a barrel shape or a double frustoconical shape periphery. The hub of the grinding disk has an opening through it of complementary shape to the periphery of the protruding of the spindle. The slit protruding portion is deformable for fitting into the hub opening, whereby the spindle and disk are fixed for rotation. Additional protrusions from the hub extending into the slits assure that the grinding disk does not rotate with respect to the spindle. The method includes disposing compressible material at both sides of the grinding disk or extending compressible material through the hole in the grinding disk, and then compressing the compressible material over the grinding disk the defining the hub for the grinding disk. In all embodiments, the protruding portion of the drive spindle and the hub are shaped so that the end of the drive spindle and the hub do not protrude significantly beyond the surface of the grinding disk and do not form an obstacle against insertion and grinding.

13 Claims, 2 Drawing Sheets

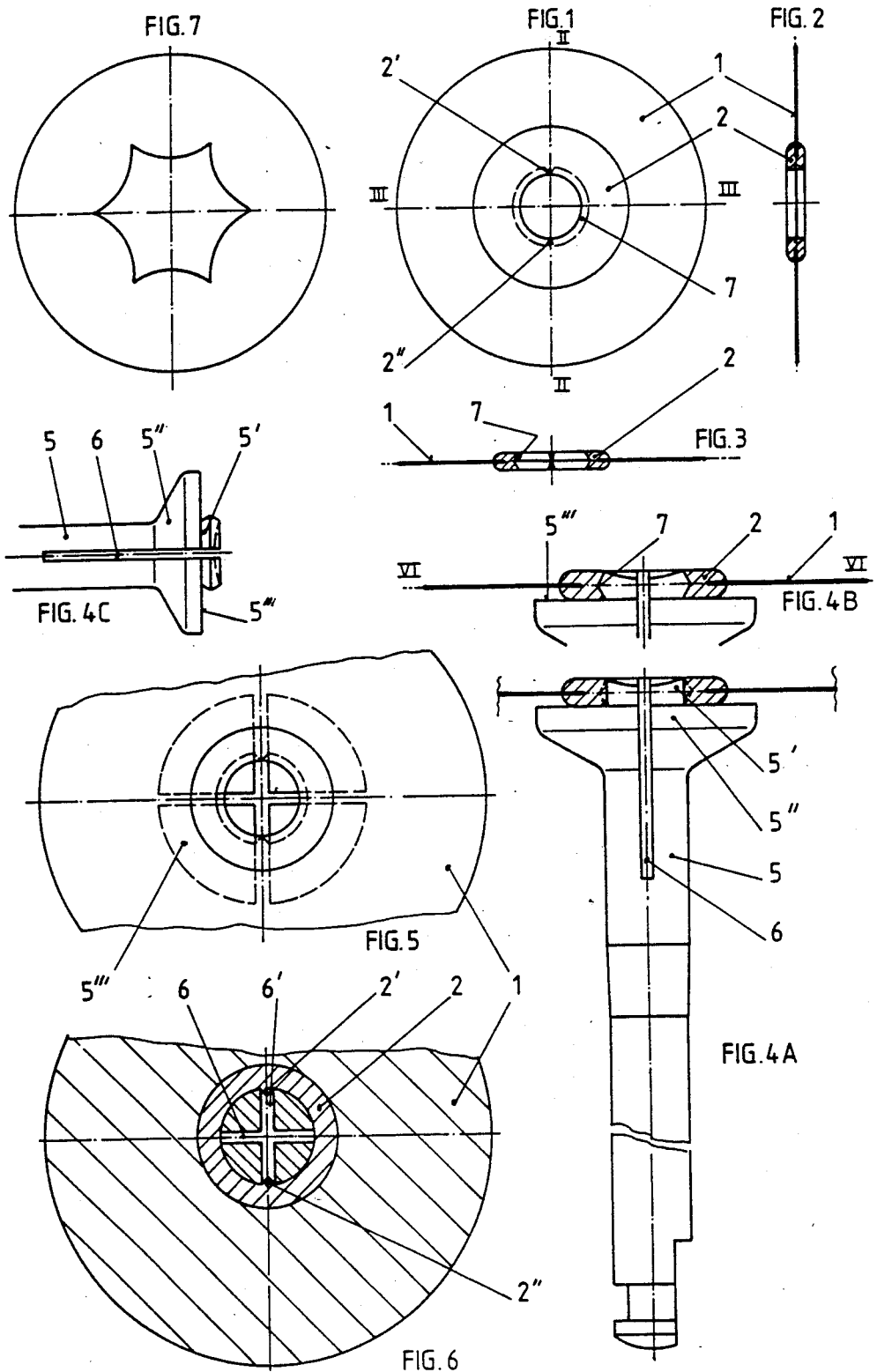

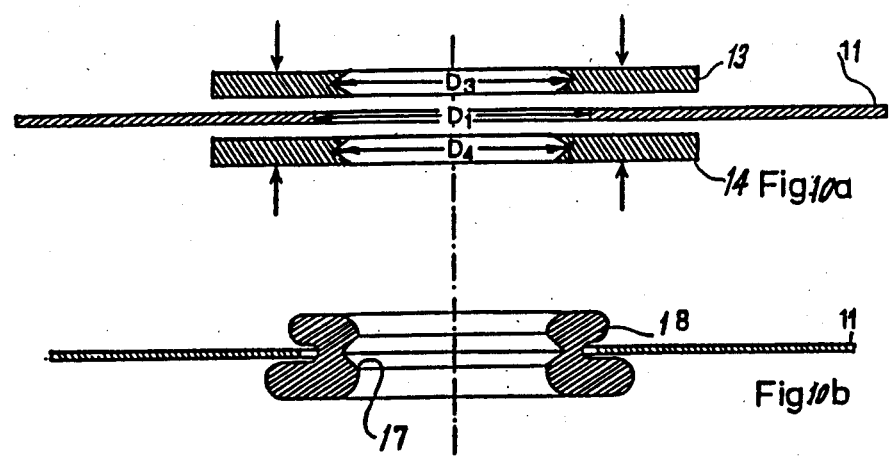
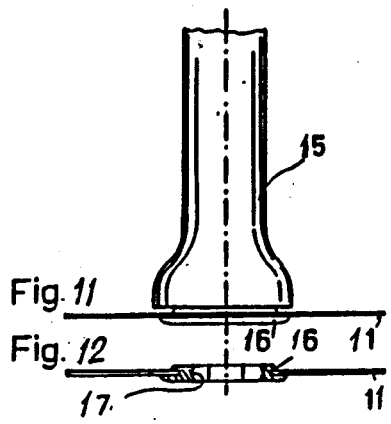
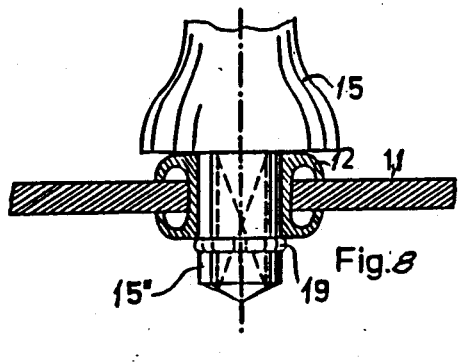
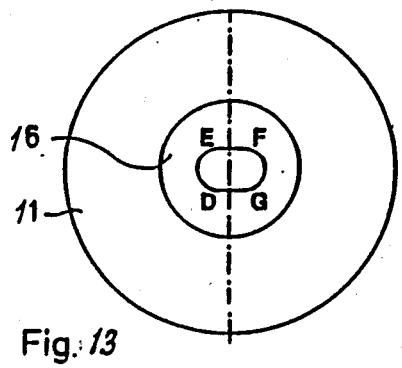
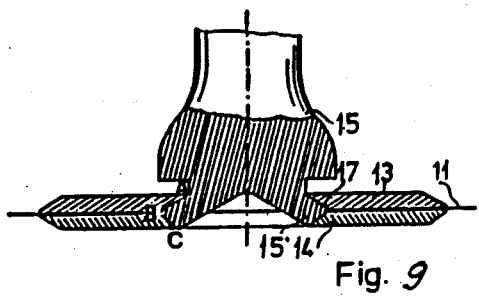

DEVICE WITH SPINDLE AND GRINDING DISK, PARTICULARY FOR DENTISTS, AND METHOD FOR THE MANUFACTURE THEREOF

The present invention concerns a device with spindle and grinding disk, in particular for dentists, as well as a method of manufacturing the grinding disk of the device.

Such devices for dentists are known, for instance, from European Patent Application No. 0,044,701 of Jan. 27, 1982.

They have the disadvantage that they do not permit maximum penetration by the peripheral region of the grinding disk into the spaces between the teeth since the free end of the drive spindle protrudes beyond the grasping disk and thus forms an obstacle.

Furthermore, the protruding spindle can damage or discolor the surface of the tooth during its rotation, particularly when plastic is concerned, such as used, for instance, also for the filling of teeth.

The device in accordance with the present invention avoids these disadvantages.

The invention will be explained below, by way of example, with reference to the drawing, in which:

FIG. 1 is a plan view of a grinding disk with its hub,

FIG. 2 is a cross section through the grinding disk along the section line II—II of FIG. 1, FIG. 3 is a cross section along the section line III—III of FIG. 1, FIG. 4A is a side view, partly in section, of the device with the drive spindle and the mounted grinding disk, FIG. 4B is a cross section through the free end of the spindle according to FIG. 4A, taken in a plane perpendicular to the plane of the drawing of FIG. 4A, FIG. 4C is a view of the free end of the spindle with the clamp to receive the grinding disk by pressure and elastic deformation, FIG. 5 is a front view of part of FIG. 4A, FIG. 6 is a part of the cross section along the section plane VI—VI of FIG. 4B, FIG. 7 is a variant of a grinding disk with axial opening for reception of the hub, in star shape, FIG. 8 is a portion of an axial section through a grinding disk placed on the end of a drive spindle in accordance with the prior art and corresponding protrusion of the free end of the spindle beyond the grinding plane of the grinding disk, FIG. 9 is a section similar to that of FIG. 8 with a flattened disappearing spindle end, in a first embodiment, FIGS. 10a and 10b are two different embodiments in line FIG. 9, FIG. 11 shows another embodiment of a spindle end with flattened end and a grinding disk with hub pressed thereon, FIG. 12 is an axial section through the grinding disk and its hub, in the embodiment shown in FIG. 11, FIG. 13 is a plan view of the grinding disk with hub, similar to FIG. 12.

In accordance with the various FIGS. 1 to 7, the device comprises a thin grinding disk 1 with its hub 2. Both of these are preferably compression molded from plastic of the same or different kinds, particularly polyesters, there is a drive spindle 5 of metal, for instance brass, stainless steel or else a flexible rigid plastic.

The free end of the spindle is divided, in accordance with the planes 6, 6', into a number of segments, for instance in two planes which are perpendicular to each other as shown, or in three planes which are spaced 120° apart from each other.

The hub has one or more projections 2', 2" which protrude into the notches 6, 6' on the free end of the spindle so as, by form lock, to prevent slippage of the disk 1 with respect to the spindle 5 even if high resistance is produced during the grinding and polishing of the teeth as a result of a high pressure of application.

The clamp 5' of the drive spindle 5 does not protrude from the hub 2, as can be clearly noted from FIGS. 4A and 4B. This has the result that no additional noticeable obstacle is created in the spaced between the teeth. Accordingly, it is possible to bring the grinding disk also to places where the spaces between the teeth are very narrow, which is not possible with the known implements.

A third feature of this device consists in the broadening 5" (FIG. 4A) of the head of the drive spindle so as thereby to create a flat resting surface 5''' against which the flat surface of the hub 2 of the grinding disk 1 comes to rest, thus assuring the completely flat application thereof. This surface is at right angles to the axis of the spindle 5, whereby oscillations and deformations of the disk in operation are avoided.

The spindle has an angled shape end 5', for instance, it is in the form of a double conical frustum, (FIG. 4C), which pushes itself into the complementary groove 7 (FIG. 4B) of the hub 2. This assures perfect flatness of the disk 2.

In order to obtain securement, the diameter of the clamp 5 (FIG. 4C) of the drive spindle is made somewhat larger than or the same size as the diameter of the complementary concave groove 7 of the hub 2.

The shapes and types of material for the parts of the device can be different.

The grinding disk described makes it possible to penetrate, in particular, into narrow, poorly accessible spaces between two teeth as a result of the special construction of the disk and Nevertheless no undesired deformation of the disk during the grinding need be feared. This penetration by the disk is caused, in particular, also by the fact that the spindle, for all practical purposes, does not protrude beyond the free surface of the. This is also true of the hub, which is connected to the grinding disk by a pressing method.

The grinding disks described are extremely thin. They have a thickness of about 0.1 to 0.5 mm and nevertheless are of a relatively large diameter so as to be able to penetrate into concealed tooth spacings.

As a special feature, polyester plastic is used for the disk hub, specifically in its elastic form. This is favorable since pressing onto the shank is facilitated and a force-locked connection between the driving shank and the driven disk or its hub is produced already in its position of rest. This prevents the grinding disk from stopping while the motor is operating, even in the case of low speeds of rotation.

FIG. 8 shows the desk hub of a grinding disk of known, customary design, fastened on the free end of the spindle.

The disk hub consists of a metal ring 12 which is bent over at its two axial ends and protrudes accordingly out of the grinding plane of the grinding disk 11, and which normally has a thickness of 0.3 to 0.5 mm.

The end 15"0 of the end of the spindle 15 is inserted under elastic pressure into the disk hub 12. For instance, an elastic clamping of a small ring 19 must then be overcome. The end of the spindle protrudes from the hub 12 of the disk and forms a noticeable obstacle which does not permit penetration of the peripheral parts of the grinding disk 11 into narrow spaces between two teeth.

In accordance with the present invention, the grinding disk 11, as shown in FIG. 9, has a very slight thickness and has a disk hub 13, 14 which is extremely flat, with an annular groove 17 which, in cross section, has an angular profile A, B, C or is semicircular, or may also be of some other shape.

The end of the spindle 15, the so-called clamp 15', has a shape which is complementary to the annular groove 17 and is developed, in particular, in accordance with the shape A, B, C in angular, semicircular or similar form so as to develop a minimal obstacle protruding from the grinding plane of the grinding disk 11 during the grinding process.

As shown in FIG. 13, the groove 17 can also have straight parts. It also need not be circular. This shape is provided in order to prevent relative movement between grinding disk and hub, on the one hand, and drive spindle 15, on the other hand.

The disk hub 13, 14 according to FIG. 9 can be produced, for instance, in the manner that two axially drilled disks 13 and 14 consisting of thermoplastic material, particularly polyester (FIG. 10a), having bore diameters $D_3$ and $D_4$ which are smaller than the diameter $D_1$ of the grinding disk 11 are used. The upper plate 13 and the lower plate 14 hold the grinding disk 11 in sandwich-like manner and the entire unit is compressed in a press (not shown) in such a manner that the disk hub 13, 14 with the annular groove 17 is produced in the manner described.

In another possible procedure a grooved ring 18 (FIG. 10b) of thermoplastic material is inserted in the bore of the grinding disk 11 in a press and the entire unit is compressed by ultrasonics in order thereby to obtain the disk hub of FIG. 9 or FIG. 11 or 12.

The disk hub in the grinding disk and that of the flattened clamp 15' of the spindle may be round, triangular, polygonal, oval, trapezoidal, etc. in shape.

The present invention can also be applied in other fields where grinding in small spaces is necessary, whether in the metal- wood- or stoneworking industry or in the watch industry or the jewelry business.

I claim:

1. A spindle and grinding disk combination comprising:
   a rotatable spindle, having an end, the spindle end being radially slit and the end being elastically deformable such that squeezing pressure applied to the spindle end can be absorbed by deflection of the spindle end at the slit; the spindle end having an outwardly facing end face, a portion of the spindle end protruding from the end face, the protruding portion also being radially slit and also having a periphery which is profiled;
   the grinding disk including a hub, the hub resting on the end face of the spindle end with the grinding disk installed on the spindle; a groove formed in the hub complementary to the peripheral profile of the protruding portion of the spindle end for receiving the protruding portion, and the hub groove being sized for the hub to grip securely on the protruding portion of the spindle end for connecting the spindle end and the disk for fixed rotation with each other.

2. The combination of claim 1, wherein the protruding portion of the spindle end has a generally barrel shaped peripheral profile.

3. The combination of claim 1, wherein the protruding portion of the spindle end has a generally double frustoconical shaped peripheral profile.

4. The combination of claim 1, wherein the protruding portion of the spindle end is comprised of elastically deformable material and it is radially slit so that the hub applied to the protruding end portion deforms the protruding end for holding the hub to the protruding end, whereby the disk and the hub are removably replaceable on the protruding end.

5. The combination of claim 4, wherein the disk has a predetermined thickness above the end face of the spindle and the protruding portion of the spindle is of a length so that it does not protrude beyond the hub of the disk with the disk hub mounted on the protruding portion.

6. The combination of claim 4, wherein the periphery of the protruding portion is shaped convexly on the periphery and the groove in the hub of the disk having a complementary concave shape for receiving the convexly protruding portion.

7. The combination of claim 4, further comprising additional protrusions at the surface of the hub placed and shaped for being received in the slit in the end face of the spindle end for preventing slipping of the hub with respect to the spindle.

8. The combination of claim 4, wherein the spindle widens toward the end face, and the end face of the spindle end comprises a flat surface perpendicular to the longitudinal axis of the spindle; the grinding disk resting at the flat surface for the disk to be disposed at right angles to the axis of the spindle.

9. The combination of claim 6, wherein the convex periphery of the protuding portion of the spindle end has an angled cross section and a diameter at least equal the diameter of the concave groove in the hub of the disk for been received in the groove of the hub.

10. The combination of claims 7, wherein the protrusions are generally triangular in shape, with the apex of a triangular protrusion radially toward the center of the hub and the base of the protrusion radially outward.

11. The combination of claim 10, wherein the end face of the spindle has an intersecting pair of slits formed therein and the protrusions are paired, with the protrusions of a pair lying opposite each other around the spindle and the projection pairs being so placed as to be received in the longitudinal slits in the end face of the spindle.

12. The combination of claim 1, wherein the hub of the grinding disk is generally as thick as the grinding disk, the disk hub having an annular recess of a shaped cross-section and the hub being prressed on to the protruding portion of the spindle end, and the protruding portion of the spindle being complementary in shape to the annular recess of the disk hub, wherein the protruding portion of the spindle is elastically deformable for being deformed to fit into and to secure the protruding portion in the recess in the hub.

13. The disk of claim 1, wherein the opening in the disk hub is non-circular in shape.

* * * * *